United States Patent [19]

Iijima et al.

[11] 4,071,475
[45] Jan. 31, 1978

[54] TRANSPARENT HIGHLY VISCOUS LIQUID SHAMPOO COMPOSITION

[75] Inventors: Eiji Iijima, Chiba; Hiroshi Watanabe, Funabashi; Shizuo Hayashi, Sugito, all of Japan

[73] Assignee: Kao Soap Co., Ltd., Tokyo, Japan

[21] Appl. No.: 722,129

[22] Filed: Sept. 10, 1976

[30] Foreign Application Priority Data

Sept. 16, 1975 Japan .................... 50-111860

[51] Int. Cl.² ............... C11D 1/14; C11D 1/83
[52] U.S. Cl. .................... 252/545; 252/548; 252/550; 252/DIG. 13; 252/DIG. 14
[58] Field of Search ....... 252/550, 548, 545, DIG. 13, 252/DIG. 14, 316

[56] References Cited

U.S. PATENT DOCUMENTS

| 2,875,153 | 2/1959 | Dalton | 252/132 |
| 2,941,950 | 6/1960 | Korpi et al. | 252/548 |
| 3,238,141 | 3/1966 | Gatza | 252/316 |
| 3,723,360 | 3/1973 | Hewitt | 252/542 |
| 3,748,276 | 7/1973 | Schmolka | 252/316 |
| 3,954,660 | 5/1976 | Kennedy et al. | 252/353 |

FOREIGN PATENT DOCUMENTS

674,896  7/1952  United Kingdom.

OTHER PUBLICATIONS

"Clear Detergent Shampoos," Soap and Chemical Specialties, vol. 30, July 1954, pp. 77 and 79.
Keithler, "The Clear Shampoo," Drug and Cosmetic Industry, Nov. 1954, pp. 610, 611, 710–713.

*Primary Examiner*—P.E. Willis, Jr.
*Attorney, Agent, or Firm*—Blanchard, Flynn, Thiel, Boutell & Tanis

[57] ABSTRACT

A transparent, highly viscous, liquid shampoo composition comprising, as critical components, (A) from about 1 to about 10% by weight of a polyoxyethylene alkyl ether having the formula (I):

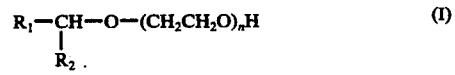

$$R_1 - CH - O - (CH_2CH_2O)_n H \quad (I)$$
$$| $$
$$R_2$$

wherein $R_1$ is alkyl having 8 to 14 carbon atoms, $R_2$ is hydrogen or alkyl having 1 to 7 carbon atoms, and n denotes the mole number of added ethylene oxide units and its distribution is as follows:

n = zero to one : up to 10%,
n = 2 to 4 : at least 90%, with the proviso that n equals 3 is at least 50%, and
n ≧ 5 : up to 10%, and (B) from about 5 to about 40% by weight of alkyl sulfate alkylolamine salt in which the carbon atom number of the alkyl group is in the range of from 11 to 15 and the carbon atom number of the alkylol group is 2 or 3.

4 Claims, No Drawings

TRANSPARENT HIGHLY VISCOUS LIQUID SHAMPOO COMPOSITION

BACKGROUND OF THE INVENTION

1. Field of the Invention

The present invention relates to a transparent, highly viscous, liquid, hair shampoo composition.

2. Description of the Prior Art

Alkylolamine alkyl sulfates are commonly employed as surfactants in liquid shampoos. This kind of surfactant has a higher foaming property and gives a better washing finish than other surface active agents, for example, sodium polyoxyethylene alkylether sulfates, 2-alkyl-N-carboxymethyl-N-carboxyethylimidazolinium betaines, nonyl phenyl ether and its sulfates.

If a shampoo does not have a suitable viscosity, it easily flows off the palm of the user's hand and the application of it is difficult. Thus, in order to increase the commercial value of shampoos, it is necessary to provide same with a suitable high viscosity. In general, a water-soluble polymer or a higher fatty acid alkylolamide is used in shampoo compositions for this purpose.

It is known that the viscosity is increased and the foaming property is enhanced if a higher alcohol or a polyoxyethylene (1-5) alkyl ether is incorporated in either alkylolamine alkyl sulfates or anionic surfactants. However, in each case, precipitation takes place at low temperatures and such compounds cannot satisfactorily be used as a component of a transparent shampoo.

SUMMARY OF THE INVENTION

We have discovered that a transparent, highly viscous, liquid shampoo can be obtained by adding a polyoxyethylene alkyl ether to an alkyl sulfate alkylolamine salt, provided that the distribution of the mole number of added ethylene oxide units in the polyoxyethylene alkyl ether is maintained within critical limits.

More specifically, in accordance with the present invention, there is provided a transparent, highly viscous, liquid shampoo composition comprising, as critical components, (A) from about 1 to about 10% by weight, preferably from 3 to 6% by weight, of a polyoxyethylene alkyl ether having the formula (I):

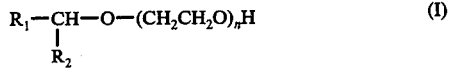

wherein $R_1$ is alkyl having 8 to 14 carbon atoms, $R_2$ is hydrogen or alkyl having 1 to 7 carbon atoms, and $n$ denotes the mole number of added ethylene oxide units and its distribution is as follows:

$n$ = zero to one : up to 10%, based on the total weight of component A, $n$ = 2 to 4 : at least 90%, with the proviso that at least 50% of the total weight of component A consists of compounds in which $n$ is 3, $n \geq 5$ : up to 10%, based on the total weight of component A, and (B) from about 5 to about 40% by weight, preferably from 8 to 25% by weight, of an alkyl sulfate alkylolamine salt in which the carbon atom number of the alkyl is in the range of from 11 to 15 and the carbon atom number of the alkylol amine is 2 or 3.

If desired, the shampoo composition of the present invention can further contain other conventional ingredients of hair shampoo compositions employed in the conventional amounts, such as, a higher fatty acid alkylolamide (1 to 5 wt.%), urea (3 to 6 wt.%), a polyol (1 to 10 wt.%) such as propylene glycol or glycerin, an antioxidant, a ultraviolet absorber, a preservative, a chelating agent, a perfume and a dye. Still further, in order to enhance the washing activity, in addition to the alkylolamine alkyl sulfate, other surfactants, for example, a sodium salt or an alkylolamine salt of a polyoxyethylene alkyl ether, sodium alkyl sulfate or sodium alkyloyl taurine can be incorporated into the shampoo composition of the present invention.

The present invention will now be described in more detail by reference to the following illustrative experiments and examples.

EXPERIMENT 1

The influence of the addition of polyoxyethylene alkyl ethers, having different mole numbers of added ethylene oxide units, on the viscosity, stability at low temperature and foaming property of a 16 wt.% aqueous solution of triethanolamine lauryl sulfate was examined.

A polyoxyethylene lauryl ether having on the average 5 moles of added ethylene oxide units (abbreviated as "EO") was rectified to obtain fractions containing zero, one, 2, 3, 4 and 5 moles of EO, respectively, as shown in Table 1. As the fraction wherein EO = zero, the starting alcohol per se was tested. Each fraction was analyzed by gas chromatography to determine its purity. The carbon atom number distribution in the alcohol was as follows:

$C_{10}$: 2.1 wt.%
$C_{12}$: 95.2 wt.%
$C_{14}$: 2.7 wt.%

Table 1

| Fraction No. | Mole number of Added Ethylene Oxide units | Content (wt.%) of compounds having the specified mole number of added ethylene oxide units |
|---|---|---|
| 1 | zero | 100 % |
| 2 | one | 98.2 |
| 3 | 2 | 96.7 |
| 4 | 3 | 95.4 |
| 5 | 4 | 96.1 |
| 6 | 5 | 95.2 |

The results of the tests are shown in Table 2.

Table 2

| Additive | Amount Added (wt.%) | Viscosity (cps) | Stability at low temperature (−5° C/1 month)* | Foaming Property** |
|---|---|---|---|---|
| Lauroyl diethanolamide | 2 | 4.7 | 0 | 0 |
|  | 4 | 7.5 | 0 | 0 |
|  | 6 | 39.5 | 0 |  |
|  | 8 | 440 | 0 |  |
| Lauryl alcohol (Fraction 1) | 2 | — | X |  |

Table 2-continued

| Additive | Amount Added (wt.%) | Viscosity (cps) | Stability at low temperature (−5° C/1 month)* | Foaming Property** |
|---|---|---|---|---|
| Lauryl glycol ether (Fraction 2) | 4 | not dissolved | X | — |
|  | 2 | 6.4 | X | 0 |
|  | 4 | 281 | X | 0 |
|  | 6 | 908 | X | — |
|  | 8 | not dissolved | X | — |
| Lauryl diethylene glycol ether (Fraction 3) | 2 | 5.3 | 0 | 0 |
|  | 4 | 33.6 | 0 | 0 |
|  | 6 | 6780 | X |  |
|  | 8 | 4400 | X |  |
| Lauryl triethylene glycol ether (Fraction 4) | 2 | 4.8 | 0 | 0 |
|  | 4 | 8.5 | 0 | 0 |
|  | 6 | 66.9 | 0 | 0 |
|  | 8 | 1058 | 0 | 0 |
| Lauryl tetraethylene glycol ether (Fraction 5) | 2 | 4.6 | 0 | 0 |
|  | 4 | 6.0 | 0 | 0–Δ |
|  | 6 | 13.5 | 0 | 0–Δ |
|  | 8 | 61.8 | 0 | 0–Δ |

Notes
*Stability at low temperature
0 transparent
X opaque
**Foaming property

A beaker having a diameter of 5 cm and a height of 130 cm was charged with 400 cc of a sample solution, one contaminated cloth sheet (wool muslin contaminated with 46 – 63 mg of lanolin alcohol) and 20 rubber balls, each having a weight of 1.6 g. The contents of the beaker were agitated at 42 rpm for 15 minutes. Ten minutes after termination of the agitation, the height of the foam was measured and the foaming property was evaluated according to the following scale.

⊚ : foam height of more than 90 mm
O : foam height of 80 – 90 mm
Δ : foam height of 50 – 80 mm
X : foam height of less than 50 mm From the results shown in Table 2, it will be understood that in the case of simple products, the viscosity can be increased, while maintaining transparency, when the mole number of added ethylene oxide units is 3 or more in the polyoxyethylene alkyl ether; the 2-mole adduct can be added in an amount up to 4%; and that in the 4-mole adduct the viscosity-increasing effect is low and the foaming property is degraded to some extent.

The 3-mole adduct is most preferred because it has a high viscosity increasing effect and provides excellent stability at low temperature and foaming property.

EXPERIMENT 2

In Experiment 1, it has been confirmed that the adduct of EO = 3 is most preferred as the viscosity increasing agent for triethanolamine lauryl sulfate. In this Experiment, there was examined the effect of the purity of the 3-mole adduct. These tests also were performed on 16 wt.% aqueous solutions of triethanolamine lauryl sulfate. The results are shown in Table 3.

Table 3

| Weight ratio of Polyoxyethylene lauryl ether | | | Total amount Added (wt.%) | Viscosity | Stability at low temperature* | Foaming Property** |
|---|---|---|---|---|---|---|
| EO=2 | EO=3 | EO=4 |  |  |  |  |
| 100 | 0 | — | 4 | 33.6 | 0 | 0 |
| 50 | 50 | — | 4 | 14.2 | 0 | 0 |
| 0 | 100 | — | 4 | 8.5 | 0 | 0 |
| 100 | 0 | — | 6 | 6780 | X |  |
| 50 | 50 | — | 6 | 425 | 0 |  |
| 0 | 100 | — | 6 | 66.9 | 0 |  |
| 100 | 0 | — | 8 | 4400 | X |  |
| 50 | 50 | — | 8 | 2100 | 0 |  |

Table 3-continued

| Weight ratio of Polyoxyethylene lauryl ether | | | Total amount Added (wt.%) | Viscosity | Stability at low temperature* | Foaming Property** |
|---|---|---|---|---|---|---|
| EO=2 | EO=3 | EO=4 |  |  |  |  |
| 0 | 100 | — | 8 | 1058 | 0 |  |
| — | 100 | 0 | 4 | 8.5 | 0 | 0 |
| — | 50 | 50 | 4 | 7.3 | 0 | 0 |
| — | 0 | 100 | 4 | 6.0 | 0 | 0–Δ |
| — | 100 | 0 | 6 | 66.9 | 0 |  |
| — | 50 | 50 | 6 | 27.2 | 0 | 0 |
| — | 0 | 100 | 6 | 13.5 | 0 | 0–Δ |
| — | 100 | 0 | 8 | 1058 | 0 |  |
| — | 50 | 50 | 8 | 292 | 0 | 0 |
| — | 0 | 100 | 8 | 61.8 | 0 | 0–Δ |

Notes
*Evaluated as described in Experiment 1.
**Evaluated as described in Experiment 1.

EXPERIMENT 3

In this Experiment, the permissible contents of adducts of EO = 1 and EO = 5 in the polyoxyethylene lauryl ether were examined by the same procedure described in Experiment 1. The results are shown in Table 4.

|  | Sample (A) | Sample (B) |
|---|---|---|
| EO = 2 | 50 % | — |
| EO = 3 | 50 % | 50 % |
| EO = 4 | — | 50 % |

Table 4

| Total Amount Added (%) | EO | | | | | Stability at low temperature* | Foaming Property** |
|---|---|---|---|---|---|---|---|
|  | 0 | 1 | 5 | A | B |  |  |
| 4 | 10 | — | — | 90 | — | X | 0 |
| 4 | — | 10 | — | 90 | — | 0 | 0 |
| 4 | 5 | 10 | — | 85 | — | X | 0 |
| 6 | 10 | — | — | 90 | — | X |  |
| 6 | — | 10 | — | 90 | — | 0 |  |
| 6 | 5 | 10 | — | 85 | — | X |  |
| 6 | — | 15 | — | 85 | — | 0–Δ |  |
| 8 | 10 | — | — | 90 | — | X |  |
| 8 | — | 10 | — | 90 | — | 0 |  |
| 8 | 5 | 10 | — | 85 | — | X |  |
| 8 | — | 15 | — | 85 | — | 0–Δ |  |
| 6 | — | — | 10 | — | 90 | 0 | 0 |
| 6 | — | — | 15 | — | 85 | 0 | 0–Δ |

Table 4-continued

| Total Amount Added (%) | EO 0 | 1 | 5 | A | B | Stability at low temperature* | Foaming Property** |
|---|---|---|---|---|---|---|---|
| 6 | — | — | 20 | — | 80 | 0 | 0–Δ |

Notes
*Evaluated as described in Experiment 1.
**Evaluated as described in Experiment 1.

From the results shown in Table 4, it will readily be understood that compound having EO = 0 to 1 or EO = 5 can be incorporated without serious disadvantage in the amounts up to 10 wt.%.

EXAMPLE 1

| | |
|---|---|
| Triethanolamine lauryl sulfate | 16.0 % by weight |
| Polyoxyethylene lauryl ether | 4.0 % by weight |
| (EO distribution: | |
| n = 0 : 0% by weight | |
| n = 1 : 3.0 % by weight | |
| n = 2 : 24.2 % by weight | |
| n = 3 : 53.3 % by weight | |
| n = 4 : 18.1 % by weight | |
| n = 5" 1.4 % by weight) | |
| Urea | 6.0 % by weight |
| Tetrasodium ethylenediamine tetracetate | 0.3 % by weight |
| Perfume and dye | small amounts |
| Deionized water | 73.7 % by weight |

A shampoo having the above composition had a high foaming property and did not lose transparency even at −5° C. The viscosity of the shampoo was 500 cps as measured at 30° C.

EXAMPLE 2

| | |
|---|---|
| Triethanolamine lauryl sulfate | 9.0 % by weight |
| Triethanolamine polyoxyethylene lauryl ether sulfate | 9.0 % by weight |
| Coconut fatty acid diethanolamide | 1.0 % by weight |
| Polyoxyethylene lauryl ether | 3.0 % by weight |
| (EO distribution: | |
| n = 0 : 0 % by weight | |
| n = 1 : 5.0 % by weight | |
| n = 2 : 12.5 % by weight | |
| n = 3 : 81.4 % by weight | |
| n = 4 : 4.6 % by weight | |
| n = 5 : 1.0 % by weight) | |
| Sodium benzoate | 0.5 % by weight |
| Tetrasodium ethylenediamine tetracetate | 0.3 % by weight |
| Perfume and dye | small amounts |
| Deionized water | 77.2 % by weight |

A shampoo having the above composition had a high foaming property and did not lose transparency even at −5° C. The viscosity of the shampoo was 430 cps as measured at 30° C.

The embodiments of the invention in which an exclusive property or privilege is claimed are defined as follows:

1. A transparent, highly viscous, liquid shampoo composition consisting essentially of
   A. from about one to about 10 weight percent of one or a mixture of compounds having the formula

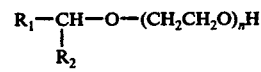

wherein $R_1$ is alkyl having 8 to 14 carbon atoms, $R_2$ is hydrogen or alkyl having one to 7 carbon atoms, and wherein
   1. $n$ is a number of from zero to one, for from zero to 10 weight percent of the total weight of component A,
   2. $n$ is a number of from 2 to 4, for from 90 to 100 weight percent of the total weight of component A, with the proviso that $n$ is 3 for from 50 to 100 weight percent of the total weight of component A, and
   3. $n$ is a number of 5 or more, for from zero to 10 weight percent of the total weight of component A;
   B. from about 5 to about 40 weight percent of alkyl ($C_{11}$ to $C_{15}$) sulfate alkylolamine ($C_2$ to $C_3$) salt, and
   C. the balance is essentially water.

2. A shampoo composition according to claim 1 wherein the amount of component A is from 3 to 6 weight percent, and the amount of component B is from 8 to 25 weight percent.

3. A shampoo composition according to claim 1 also containing from one to 5 weight percent of a higher fatty acid alkylolamide, or from 3 to 6 weight percent of urea, or from one to 10 weight percent of propylene glycol or glycerin, or combinations thereof.

4. A shampoo composition according to claim 1 in which component A is polyoxyethylene lauryl ether and component B is triethanolamine lauryl sulfate.

* * * * *